United States Patent [19]

Borghard et al.

[11] Patent Number: 4,762,010
[45] Date of Patent: Aug. 9, 1988

[54] APPARATUS AND METHOD FOR ADSORPTION AND DESORPTION STUDIES, PARTICULARLY FOR CHARACTERIZATION OF CATALYSTS

[75] Inventors: William S. Borghard, Yardley, Pa.; Hans J. Schoennagel, Pennington, N.J.

[73] Assignee: Mobil Oil Corporation, New York, N.Y.

[21] Appl. No.: 33,150

[22] Filed: Apr. 2, 1987

[51] Int. Cl.[4] .............................................. G01N 15/08
[52] U.S. Cl. ........................................ 73/865.5; 73/38
[58] Field of Search ................................. 73/865.5, 38

[56] References Cited

U.S. PATENT DOCUMENTS

| | | | |
|---|---|---|---|
| 2,729,969 | 1/1956 | Innes | 73/38 |
| 3,262,319 | 7/1966 | Orr et al. | 73/865.5 |
| 3,349,625 | 10/1967 | Benusa et al. | 73/865.5 |
| 3,464,273 | 8/1969 | Hendrix et al. | 73/865.5 |
| 3,555,912 | 1/1971 | Lowell | 73/865.5 |
| 3,707,870 | 1/1973 | Herve et al. | 73/38 |
| 3,732,736 | 5/1973 | Glaude et al. | 73/865.5 |
| 3,771,367 | 11/1973 | Lowell et al. | 73/865.5 |
| 3,850,040 | 11/1974 | Orr et al. | 73/865.5 |
| 3,938,384 | 2/1976 | Blair | 73/204 |
| 4,487,213 | 7/1985 | Pieters et al. | 73/204 X |
| 4,496,249 | 1/1985 | Lee et al. | 73/204 X |
| 4,528,850 | 7/1985 | Witier | 73/865.5 |
| 4,566,326 | 1/1986 | Lowell | 73/865.5 |

FOREIGN PATENT DOCUMENTS 1057798 5/1959 Fed. Rep. of Germany .
1202540 10/1965 Fed. Rep. of Germany .

OTHER PUBLICATIONS

Brunauer, Emmett and Taylor, "Adsorption of Gases in Multi-Molecular Layers", *J. Amer. Chem. Soc.*, 60, 309 (1938).
Brochure, Numec Instruments and Controls Corp., "Adsorption Flow Apparatus for Particle Surface Area Determinators".
Bosch and Peppelenbos, "Automatic and Low Cost Determination or BET Surface Areas", *Journal of Physics E: Scientific: Instruments*, 10, 605–608 (1977).
Bhat et al, "A Simple Continuous Flow Apparatus for the Determination of Surface Area of Powders", *Indian Journal of Technology*, vol. 14, pp. 170–171 (Apr. 1976).
Farey et al, "Determination of Surface Areas by an Improved Continuous Flow Method", (1971), *Analytical Chemistry*, vol. 43, No. 10 (1807–1810).
Nelsen et al, "Determination of Surface Area—Absorption Measurements by a Continuous Flow Method", *Analytical Chemistry*, vol. 30, No. 8, pp. 1387–1390 (1958).

(List continued on next page.)

Primary Examiner—Stewart J. Levy
Assistant Examiner—Joseph W. Roskos
Attorney, Agent, or Firm—Alexander J. McKillop; Michael G. Gilman; Charles J. Speciale

[57] ABSTRACT

A sample is disposed in a sample chamber and is connected by a flow restrictor or "leak" to a bulb of known volume. In adsorption studies, an on/off valve is opened, allowing gas to flow from the bulb into the sample chamber. The leak controls the rate of flow to be less than the equilibrium rate of adsorption/desorption of gas with respect to the sample, such that the pressure in the sample chamber at all times is an equilibrium value. The pressure in the bulb and in the sample chamber are both measured repetitively. The change in pressure in the bulb provides an indication of the net amount of gas admitted to the sample chamber. This quantity together with the change in pressure in the sample chamber can be used to provide an indication of the amount of gas which is adsorbed onto the sample. In desorption studies the bulb is evacuated relative to the sample chamber. The on/off valve is opened to allow gas to flow from the sample chamber into the bulb at a rate controlled by the leak to be less than the equilibrium rate of adsorption/desorption such that the pressure within the sample chamber is at all times an equilibrium value. Points on the adsorption and desorption isotherms can thus be determined continually.

37 Claims, 6 Drawing Sheets

OTHER PUBLICATIONS

Farrauto, "Determination and Applications of Catalytic Surface Area Measurements", *AICHE Symposium Series*, No. 143, vol. 70, pp. 9–22 (undated).

Dollimore et al, "The BET Method of Analysis of Gas Adsorption Data and It's Relevance to the Calculation of Surface Areas", *Surface Technology*, No. 4, 121–160 (1976).

Stock, "Determination of Surface Area by Gas Chromatography", *Analytical Chemistry*, vol. 33, No. 7, 966–967 (1961).

Daeschner et al, "An Efficient Dynamic Method for Surface Area Determinations", *Analytical Chemistry*, vol. 34, No. 9, pp. 1150–1155 (1962).

Kremen et al, "A New Approach to Surface Area Determinations by Selective Gas Adsorption in a Nitrogen Helium System", delivered at the Pittsburgh Conf. on Anal. Chem. and Applied Spectroscopy (1965), pp. 1–15.

Brochure, Strohlein, "Area-Meter-Measurement of Surface Area of Powders".

Stevenson et al, "Automatic Control of Pore Size Distribution Measurement in Solids", *J. Sci. Inst.*, vol. 44, pp. 922–925 (1967) (incomplete copy).

ADSORPTION
CONTINUOUS MODE

ADSORPTION
PULSE MODE

DESORPTION
CONTINUOUS MODE
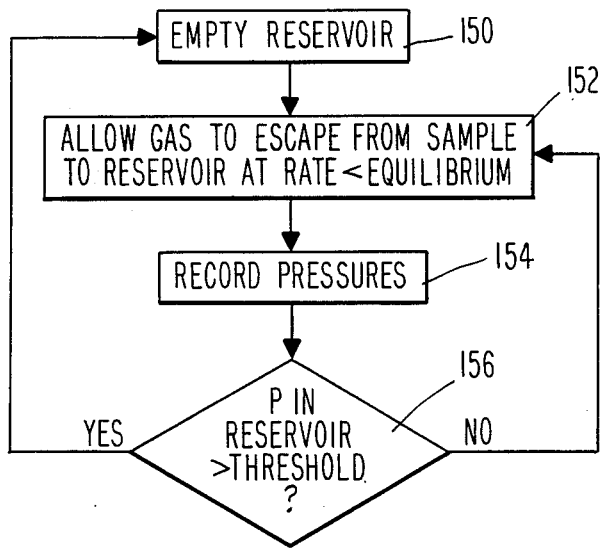
_Fig. 7_
DESORPTION
PULSE MODE
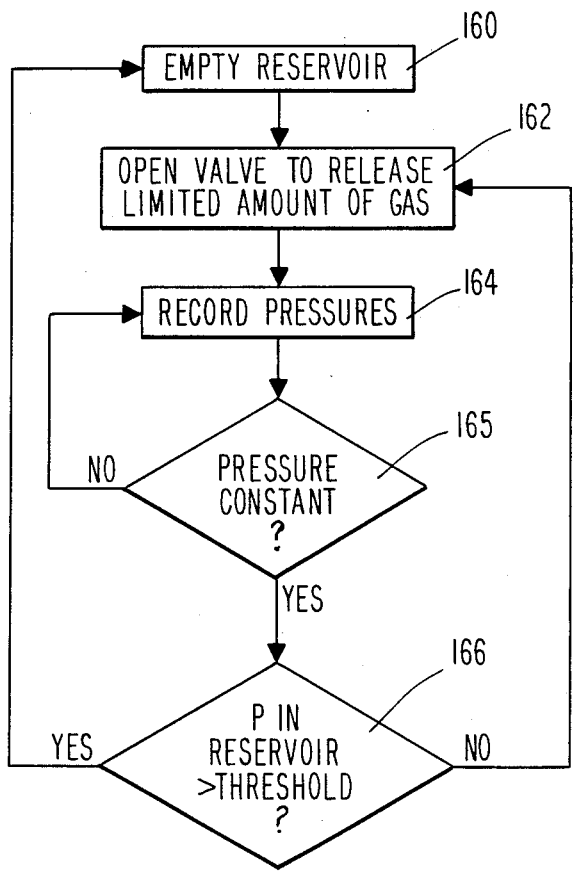
_Fig. 8_

DESORPTION
LOW PRESSURE MODE

DESORPTION
CONSTANT PRESSURE MODE

APPARATUS AND METHOD FOR ADSORPTION AND DESORPTION STUDIES, PARTICULARLY FOR CHARACTERIZATION OF CATALYSTS

FIELD OF THE INVENTION

This invention relates generally to adsorption and desorption studies aimed at measurement of the surface area and the pore size distributions of solids, which is of particular interest in connection with finely divided materials, such as powders and granular materials. Such measurements are useful in characterizing many useful products, such as pigments, various materials used in the chemical, pharmaceutical, agricultural and cosmetic industries, catalysts, and other products.

BACKGROUND OF THE INVENTION

The term "Catalyst characterization" is used herein to refer to characterization of catalysts by their pore size, pore volume, pore shapes, compaction, surface area, and other parameters which describe the catalyst structure itself, and also to measurement of the characteristics of the catalyst after use. For example, over time in oil refinery operations some fraction of the pores of a catalyst will become "clogged" with coke or other materials. The amount of this clogging is highly significant to evaluation of the continued efficient use of the catalyst.

Typical catalyst structures vary in overall dimensions from on the order of millimeters to on the order of angstroms. Most prior work in this field has involved investigation of the larger dimensions. Characterization of catalysts having extremely large surface areas and small pore sizes, for example down to five angstroms, is of particular present interest, as these are typical dimensions of zeolitic catalysts. In order to characterize catalysts having such extremely small pores, apparatus for measuring the surface areas of such catalysts is required, because these measurements provide an indication of the pore size and structure. As will appear below, presently available devices do not satisfy the needs of the art.

While the present specification describes the present invention largely in connection with the measurement of the surface area of catalysts, it should be remembered throughout that the techniques discussed herein and the claims appended hereto are not to be so limited.

The basic reference which appears to have precipitated the development of modern surface area determination techniques and accompanying catalyst characterization work is Brunauer, Emmett and Teller (hereinafter "BET"), "Adsorption of Gases in Multi-molecular Layers", *J. Amer. Chem. Soc.* 60, 309 (1938). In this work there is described the so-called BET equation (eq. A., p. 312) which quantitatively relates the amount of a gas adsorbed on the adsorbent to the partial pressure of the gas in the chamber containing the adsorbent. Specifically, if the amount of gas admitted to the chamber is known, the surface area of the adsorbent can be calculated from the amount adsorbed, which is a function of the partial pressure, using the BET equation.

Physically, as gas enters an evacuated chamber containing an adsorbent, the molecules of the gas are preferentially attracted to the adsorbent by van der Waals forces, such that the gas pressure in the chamber is less than it would have been if a similar amount of gas had been admitted to a similar chamber not having the adsorbent therein. The difference is proportional to the number of molecules of the gas adsorbed on the adsorbent. If a fixed amount of gas is admitted to an evacuated chamber containing an adsorbent at a fixed temperature, the pressure in the chamber will first abruptly rise and will then gradually decrease, until an equilibrium point is reached. At this point, the rates of adsorption and desorption of the gas molecules are equal.

The equilibrium point is a single point on a so-called adsorption isotherm for that particular material, that is, it is a point on a curve which relates the amount of gas adsorbed to the partial pressure of the gas in the chamber at a fixed temperature. If one subsequently admits an additional amount of gas to the chamber, another equilibrium will be reached, determining a second point on the isotherm, and so on. In this way certain constants appearing in the BET equation can be determined. These constants can be used to calculate the surface area of the solid according to procedures well described in the literature. See, for example, U.S. Pat. No. 3,850,040 to Orr et al.

In certain ranges of partial pressures, and given that certain other experimental conditions are controlled, the surface area of an adsorbent can be inferred from a single point on a portion of the isotherm known to be linear. As mentioned, such a point can be determined by admitting a known amount of gas to a sample chamber having a known volume, monitoring the pressure until it reaches a constant value, that is, until equilibrium is reached, and calculating the amount of gas adsorbed therefrom. The BET equation can then be used to derive a value for the surface area of the adsorbent.

One manner in which the amount of gas admitted can be determined is to connect the sample chamber to a chamber of known volume containing the gas to be adsorbed. After a valve connecting the chambers has been opened momentarily to admit a "pulse" of gas into the sample chamber, the amount of gas actually admitted can be determined by noting the change in gas pressure in the chamber of known volume and by application of the ideal gas laws. This is taught by Orr et al.

Another method of determining the amount of gas admitted is to admit the gas at a known flow rate, the flow rate having been accurately calibrated, and measure the amount of time required for a particular equilibrium partial pressure to be reached. A point on the isotherm can then be calculated using the amount of gas admitted, determined from the known flow rate and time. This method is described in U.S. Pat. No. 2,729,969 to Innes. The Innes method was apparently employed in an instrument at one time sold commercially by the Numec Instruments and Controls Corporation of Apollo, Pa., and described in a Numec brochure entitled "Adsorption Flow Apparatus for Particle Surface Area Determinations," which is known to the inventors. Additional points on the isotherm can then be determined using the Innes method as well, provided all else remains equal, so that one can derive the entire isotherm.

The above methods may be referred to as "single point" or "discontinuous" methods, in that only a single point on the isotherm is determined in a given experimental run. Another possibility is to derive more than one of the points on the isotherm in a single run. Multiple ponts on the isotherm can be located by calculating the fraction of the total adsorption sites on the adsorbent covered at any given moment as a function of the net amount of gas admitted to the chamber versus the pressure in the chamber at any given moment. To do so one must ensure that the pressure in the chamber containing the adsorbent is always at equilibrium. Equilibrium occurs when the rates of adsorption and desorption are equal. For the process just discussed to function, the rate of gas flow into the chamber must be less than what is termed herein the "equilibrium rate of adsorption/desorption"; that is, the rate of gas flow into the chamber must be sufficiently slow that if gas flow were terminated no additional net absorption would occur thereafter.

Bosch and Peppelenbos, "Automatic and Low Cost Determination of BET Surface Areas," *Journal of Physics E: Scientific Instruments,* 10, 605–608 (1977), describe an apparatus in which the latter course is followed. Bosch et al. show use of a capillary of 0.3 meters length and inside diameter of 0.1 millimeter to maintain the rate of flow of gas supplied at atmospheric pressure into an initially evacuated adsorption chamber constant and below the maximum rate of adsorption on the adsorbent. Bosch et al. indicate that the flow rate is assumed to be constant after performance of a calibration run. Id. at page 606. The amount of gas admitted is determined by multiplying the flow rate by the time of flow. Bosch et al. teach that the partial pressure within the evacuated chamber can be assumed to be at equilibrium throughout the experiment. Id. at pages 607–608. Bosch et al. can then determine a number of points on the isotherm in a single experimental run. This is a significant improvement over the method of Innes, for example, which provides a single point on the isotherm per experimental run.

There are certain significant limitations on the apparatus of Bosch et al. Bosch et al. acknowledge that the flow rate provided by their capillary is only constant to within about 0.6% and only over changes in the back pressure between 0 and 8 kPa, that is, between 0 and about 60 Torr. This is insufficient as to both accuracy and useful range. Flow rate varies even further as the partial pressure increases, leading to further inaccuracies. In effect this limits the range of pressures which can be investigated using the Bosch et al device.

U.S. Pat. No. 4,487,213 to Pieters et al provides an improvement on the Bosch et al. apparatus which amounts to an improved flow controller. The Pieters et al. flow controller comprises a capillary tube having two electrically resistive wires wrapped around its ends. A current is passed through both wires to heat gas flowing through the capillary. The gas entering the tube cools the wire at the inlet end of the tube, so that the wire at the outlet end of the tube is warmer than the wire on the inlet end of the tube. The resistance of the wire on the outlet end is therefore higher. This difference in resistance can be measured and used to determine the amount of gas flowing through the tube, as the degree of heating of the gas (and hence the difference between the resistance of the two wires) is proportional to the mass flow therethrough. The resulting flow signal can be used to control a throttling valve to control the gas flow in a simple feedback arrangement.

As mentioned above, the improvement made by Pieters et al. to the science of surface area measurement, as described in their patent, lies in the improvement in the constancy of the gas flow rate. The patent asserts that flow rate control to within about ±0.15% over a wide range of pressure differentials is possible using the improved flowmeter. This compares with a flow rate consistency of ±0.6% over a narrow range of back pressures as reported by Bosch et al.

It will be appreciated from the description above that the Pieters et al. mass flowmeter requires thermal contact between the gas and the conductive wires by way of the wall of the capillary. This fact is an important limitation on the Pieters et al. flow meter, in that it requires a minimum inlet pressure of about 15 Torr to function. The device therefore is simply not useful for performing experimental work in areas of relatively low inlet pressure. In essence this is due to the fact that at low pressures the walls of the capillary conduct heat faster than does the gas passing therethrough, such that one cannot accurately measure the flow rate of the gas.

Another drawback of the Pieters et al. flowmeter is that it must be calibrated for operation using a given gas, as the thermal conductivity of gases varies widely. Therefore, prior to sample analysis, the gas to be adsorbed is allowed to flow into an empty chamber. The volume of gas admitted can be accurately calculated from the change in pressure over time. This information together with the time required is sufficient information to calibrate the device. In subsequent operations using the particular gas, Pieters et al. must then assume that no significant changes in the relevant experimental parameters take place. Furthermore, of course, the requirement of calibration for each sample gas prevents Pieters et al. from using differing gases for various portions of the analysis, which is sometimes of analytical interest.

There are thus two basic techniques for determining surface areas of adsorbents. The first involves admission of a known amount of gas into a sample chamber at a rate far exceeding the equilibrium rate of adsorption/desorption, such that thereafter the pressure in the chamber containing the adsorbent varies over time; when it stabilizes, the equilibrium pressure has been reached, and a point on the isotherm may be determined. A refinement of this is shown in Innes, wherein the flow rate of gas into the chamber is kept below the equilibrium rate, such that one can calculate the amount of gas adsorbed simply by determining the total amount admitted, which is equal to the unit flow times the admission time, and subtracting the fraction not adsorbed, which is readily determined from the pressure in the vessel. As mentioned this method is only as accurate as the control of the gas flow rate.

The approach taken by Bosch et al. and later by Pieters et al. is somewhat different, in that a continuous flow of gas is permitted and the partial pressure is monitored continuously, such that a number of points on the isotherm can be determined in succession. However, Bosch et al. and Pieters et al. require that the flow can be constant, such that the net volume of gas admitted can be calculated, just as did Innes. It will be appreciated that all of these methods suffer from the sufficient limitation that it is not possible to measure or control mass flow rate accurately. This is particularly the case in the extremely low flow rate and partial pressure ranges of interest in connection with characterization of zeolitic catalysts.

The preceding discussion has focused largely on adsorption of a gas onto an adsorbent. In such experiments the sample is initially located within an evacuated chamber and gas is admitted thereto; if the complete isotherm is desired, gas is admitted until the partial pressure is unity, such that the gas begins to liquefy. One can then plot the relative pressure versus the amount of gas adsorbed, yielding an adsorption isotherm.

Despite the limitations posed by the Pieters et al. flow controller, almost the entire adsorption isotherm for certain gases can be plotted at certain temperatures using their approach. This is because as long as the pressure on the upstream side of the mass flow controller is greater than about 0.02 atmosphere, that is, 15 Torr, its capillary will be "filled" with gas molecules, such that a meaningful measurement will be provided. The flow rate itself can be controlled by a throttling valve located at the outlet end of the mass flow meter. Thus, even extremely low partial pressure regions on the adsorption isotherm can be explored using the Pieters et al. device.

However, the situation is different in desorption. Desorption analysis begins with a sample which, for example, is at least partially saturated with the desorbate. One then gradually removes the atmosphere above the sample. Plotting the relative pressure in the chamber versus the amount of gas desorbed yields a desorption isotherm. Desorption isotherms are extremely significant technically in that they are highly relevant to analysis of pore sizes.

The Pieters et al. patent discloses that the same mass flow controller and in particular the same mass flowmeter can be used in desorption and adsorption studies. However, at the end of the desorption curve, when the partial pressure in the sample chamber drops to less than about 0.02 atmospheres, the Pieters et al. device ceases to function for the reason mentioned above, that is, because the capillary tube of the mass flow meter is not sufficiently filled with gas molecules to provide a measurable temperature gradient. Pieters et al. candidly acknowledge this in their patent, at column 33, line 58.

As indicated above, the conventional BET technique involves measurement of the partial pressure $p/p_o$ of the gas in the chamber containing the adsorbent, that is, the actual pressure p divided by the pressure $p_o$ at which the gas liquefies. The most typical experimental techniques involve cooling the sample in a tube in a bath of liquid nitrogen at atmospheric pressure, i.e. such that $p_o$ is approximately equal to 760 Torr. The limitation on the Pieters et al. flowmeter to relative pressures greater than about 0.02 therefore means that it is functional in desorption analysis, using nitrogen as the desorbed gas, at absolute pressures above about 15 Torr. Hence most of the nitrogen desorption isotherm can be measured, although it should be noted that the lower portions of the isotherm, which cannot be explored with the Pieters et al. device, are of great interest.

However, it is frequently desired to use other gases, such as methane, ethane, hexane, benzene and other hydrocarbons, which have much higher boiling points, as desorbates. If these gases are used in connection with a sample at a convenient temperature, most of the desorption occurs at pressures below the useful range of the Pieters et al. flowmeter. For example, hexane liquefies at approximately 80 Torr at room temperature. Therefore, an extremely significant portion of its desorption curve involves absolute pressures less than 15 Torr at room temperature. Hence, the Pieters et al. method and apparatus are not useful in desorption analysis using such desorbates. Higher carbon number hydrocarbons boil at even higher temperatures, exacerbating the problem.

Nor is performing the analysis at higher sample temperatures a viable alternative; accurate temperature control is difficult, and chemical reactions between the desorbate gas and sample tend to take place (e.g., coking) which fatally impair the accuracy of the experimental data.

Inasmuch as it is clearly an objective of any laboratory equipment to be as versatile as possible, this limitation on the desorption analysis capabilities of the Pieters et al. device is extremely significant. In fact, this may preclude use of the Pieters et al. apparatus in desorption studies of zeolite-range pores, which studies are of great present interest.

OBJECTS OF THE INVENTION

It is therefore an object of the invention to provide an apparatus for adsorption and desorption studies, that is, for analysis of surface areas and pore structures of materials, which is extremely versatile with respect to the partial pressure ranges which can be explored and to the gases which may be used as adsorbates and desorbates.

It is a further object of the invention to provide an improved apparatus for surface area determination which allows variation of the gas used as adsorbate or desorbate during a run, as desired.

It is a further object of the invention to provide an apparatus for performing surface area determination for use in catalyst characterization and in characterization of other finely divided materials which does not involve measurement of the flow rate of a gas in order to calculate the amount of the gas admitted to a sample chamber, nor calibration of a flowmeter or flow controller.

It is a further object of the invention to provide an apparatus for the characterization of catalysts or other materials, particularly with respect to their surface areas, which can be readily assembled from generally available items of equipment and which is readily adaptable to substantially complete computer control of its operation.

It is a further object of the invention to provide an apparatus and method for performing adsorption and desorption studies of gases having relatively high boiling points at very low partial pressure ranges, while permitting such analysis to be performed at convenient temperatures.

It is a further object of the invention to provide an apparatus for performing adsorption and desorption studies in connection with catalyst characterization as well as characterization of other materials, and which permits operation thereof in a number of differing modes, selected by an operator, for study of various material characteristics.

SUMMARY OF THE INVENTION

The above needs of the art and objects of the invention are satisfied by the present invention, which provides an apparatus for performing adsorption and desorption studies which eliminates any form of measurement or control of the mass flow rate. As arranged for adsorption studies, the apparatus of the invention comprises a first fixed volume reservoir or "bulb" of gas. At the beginning of an experiment, this gas is at a relatively low pressure, for example, 1–10 Torr. This is connected by way of an on/off valve and a flow restrictor or "leak" to a second fixed volume sample chamber which contains the adsorbent sample. The sample chamber is evacuated at the beginning of the run. The partial pressures on both sides of the leak are continuously monitored by highly accurate pressure transducers, which are currently available. The on/off valve is opened to begin a run. The leak permits the pressures in the bulb and sample chamber to gradually equilibrate over time. The leak includes an orifice sized such that the rate of gas flow into the chamber containing the adsorbent is much less than the equilibrium rate of adsorption/desorption of the gas with respect to the sample. The amount of gas which has been admitted to the sample chamber at any time may be calculated by noting the change in pressure in the bulb and by application of the gas laws. Because at all times the partial pressure in the sample chamber is an equilibrium pressure, one can calculate points on the adsorption isotherm directly from the partial pressure.

Over a period of time, on the order of minutes, the pressures in the two chambers will gradually become nearly equal. The first chamber is then recharged to a slightly higher pressure, and the process is repeated. The starting pressure in the sample chamber at the beginning of the second run will be equal to its final pressure after the first run, and so forth. Eventually, the partial pressure in the sample chamber will reach unity, and the gas will begin to condense. At this point the entire adsorption isotherm can be graphed.

The leak is an important element in the apparatus of the invention, and must be capable of limiting the gas flow rate to a rate below the equilibrium rate of adsorption/desorption at all times during the running of the experiment. Such devices are commercially available for use in mass spectrometry and other applications where extremely low, though uncontrolled, flow rates are required. During a typical experimental run, the pressure drop across the leak may vary by a factor of perhaps 10. Hence the flow rate across the leak will also vary by a factor of 10 or more.

A highly significant advantage of the method of the invention is that the actual flow rate is irrelevant to the experimental result. It is only important that the flow rate be less than the equilibrium rate of adsorption/desorption, so that the partial pressure in the sample chamber is at all times an equilibrium pressure. The inventive method thus allows measurements of adsorption and desorption characteristics at extremely low partial pressures, such that, for example, zeolite characteristics can be effectively explored. By avoiding the need to control the flow rate, which is technically impossible at many of the low partial pressures of interest, particularly in connection with studies of the desorption of certain hydrocarbons by zeolites, and relying instead on accurate determination of the pressure in the two chambers, the device of the invention can be expected to yield significantly improved results.

As described above, the Pieters et al. device is particularly poorly adapted for use in connection with desorption analysis, because the flow meter required by this device does not operate at low inlet pressures, such as are experienced at the lower end of the desorption curve. This problem is particularly exacerbated in the case of desorption analysis using higher boiling point hydrocarbons, in which a very large proportion of the overall desorption curve can not be determined due to these limitations. The apparatus of the present invention is useful at pressures down to $10^{-5}$ Torr and in connection with essentially any adsorbate or desorbate gas.

The apparatus of the invention operates equally well in adsorption and in desorption, and is not sensitive to the boiling point of the desorbate. In desorption, the sample chamber is connected by way of the on/off valve and leak to a bulb of known volume which is then simply evacuated to a given pressure. The on/off valve is then opened; over time, the pressures in the two chambers tend to equilibrate as gas is desorbed from the sample. The leak is set such that the rate of gas flow out of the sample chamber is less than the rate of desorption, such that the partial pressure in the sample chamber is at all times an equilibrium pressure. By comparison of the changes in pressure in the two chambers, one can calculate the amount of gas desorbed, from which one can derive individual points on the desorption isotherm. Because the flow rate is not controlled other than to be below the equilibrium rate of desorption, the difficulties described above with respect to the Pieters et al. device are avoided. In effect the apparatus of the invention eliminates control of the flow rate, which is very difficult, in favor of monitoring pressure, which can be accomplished more easily and much more accurately.

As described above, in general, the apparatus of the invention is to be operated in a continuous flow mode in which a leak controls the rate of a continuous flow of gas into the sample chamber to be less than the equilibrium rate of adsorption/desorption on the sample. In this way, the pressure in the chamber is at all times an equilibrium pressure. Similarly, in desorption, the rate of withdrawal of gas is less than the equilibrium rate of desorption, such that the pressure in the chamber is always an equilibrium pressure.

It will also be possible and sometimes desirable, however, to operate the inventive apparatus in a discontinuous or "pulse" mode. In adsorption, for example, a bulb containing a known volume of gas is connected to the sample chamber by an on/off valve; no leak need be provided. The on/off valve is opened for a short period of time, during which gas enters the sample chamber at a rate much greater than the rate of adsorption. The on/off valve is then closed. While the valve is open, naturally the pressure in the sample chamber rises at a high rate; when it is closed, the pressure gradually drops as gas is adsorbed. Eventually, the pressure reaches a constant level, indicating that an equilibrium value has been reached. The amount of gas admitted (determined by noting the change of pressure in the bulb) and the partial pressure in the sample chamber can then be used to determine a point on the isotherm.

It will be appreciated that while the pressure in the sample chamber may be monitored by measuring it at intervals of time, and while, for example, the time derivative of the pressure might conveniently be monitored to determine when the pressure has equilibrated, the time required for this to occur is not itself relevant to the determination of a point on the absorption isotherm. The variation in pressure with time may be studied, however, for example, for analysis of the rate of diffusion of the adsorbate gas into the pore structure of the sample, which is of great practical significance.

The "pulse" method may also be occasionally useful in desorption as well. In such case, the bulb is evacuated and is connected by way of an on/off valve to a sample chamber containing a sample having a gas adsorbed thereon. The valve is opened for a short period of time. Some fraction of the gas in the sample chamber above the sample passes through the valve into the bulb. After the valve is closed, the change in pressure in the bulb can be used to determine the amount of gas removed from the sample chamber. The pressure in the sample chamber drops abruptly while the valve is open; after it is closed, the pressure gradually rises as gas is desorbed, until the pressure equilibrates. A point on the desorption isotherm can then be determined. Again, the time taken is not relevant to location of this point, although it may have relevance in pore characterization as described above.

Other details and aspects of the invention will be apparent to those of skill in the art from the detailed discussion thereof which is provided below.

BRIEF DESCRIPTION OF THE DRAWINGS

The invention will be better understood if reference is made to the accompanying drawings, in which:

FIG. 7 shows a flowchart of the steps perfomed according to the invention in performance of desorption studies in the "continuous" mode;

FIG. 8 shows a flowchart of the steps performed according to the invention in desorption studies in the "pulse" mode;

DESCRIPTION OF THE PREFERRED EMBODIMENTS

Figure 2:
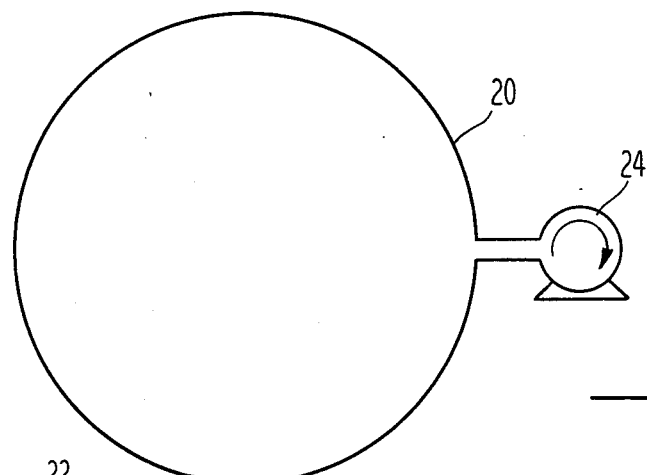
FIG. 2 shows a schematic view of the apparatus of the invention, as arranged for desorption studies.
Figure 1:
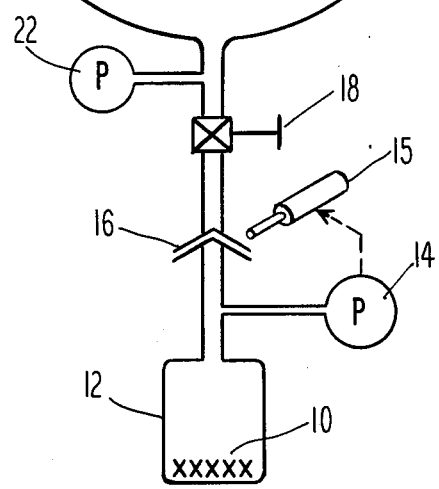
FIG. 1 shows a schematic view of the apparatus according to the invention, as used for adsorption studies.
Figure 1:
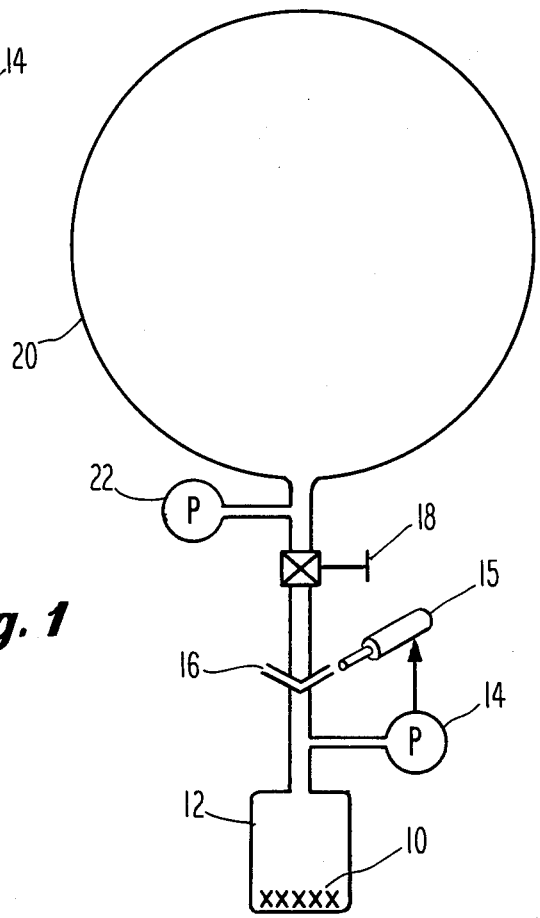
Figure 3:
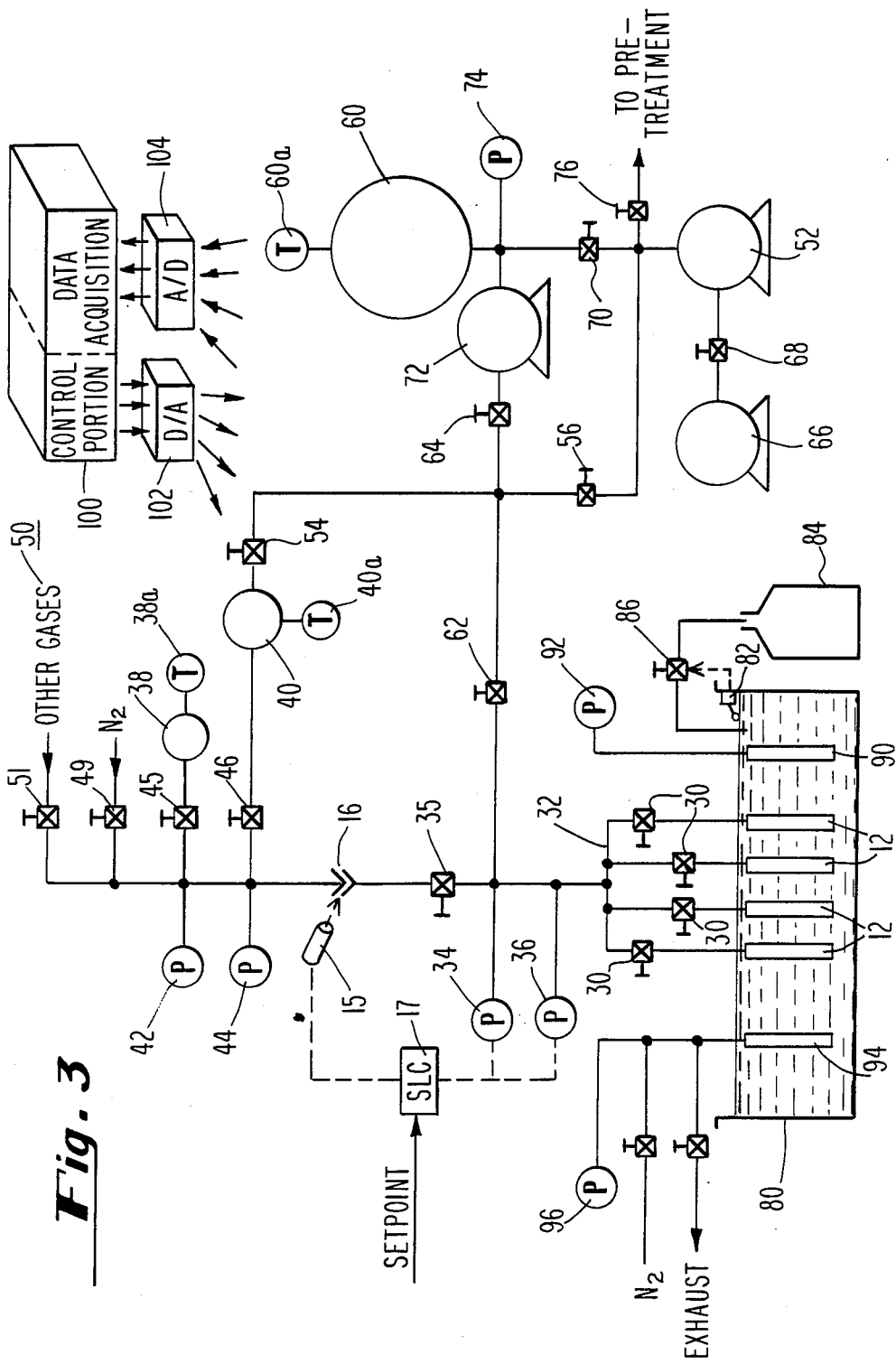
FIG. 3 shows an overall schematic view of the apparatus of the invention.

For convenience in understanding this invention, the following description of its preferred embodiments first describes its basic elements and the basic theory of its operation in the adsorption mode, in connection with FIG. 1. FIG. 2 and the discussion thereof similarly illustrate operation of the apparatus in the desorption mode. FIG. 3 shows a relatively detailed schematic view of the complete apparatus, which with the discussion thereof illustrates the manner in which the same apparatus is used for both adsorption and desorption analysis.

FIG. 1 shows, as mentioned, a schematic view of the apparatus of the invention as employed in adsorption experiments. A sample 10, which may be prepared according to any one of a wide variety of well known techniques, is disposed in a sample chamber 12. The pressure in the sample chamber 10 is measured by a pressure transducer 14, which in the preferred embodiment is a highly accurate pressure sensing unit with the capability of being remotely monitored by a computer device or the equivalent. Such transducers are available from the MKS Instruments Co. of Burlington, MA. A flow restrictor or "leak" 16 is connected to the sample chamber by a conduit. The leak 16 is essentially a throttling valve. In the preferred embodiment leak 16 may be variable, that is, may define an orifice which can be changed. This variation can be performed directly by an operator or under computer control, for example, by way of a stepper motor 15 arranged to turn a vernier screw moving a lever controlling motion of a valve member. For example, a suitable variable leak 16 may be the model 951-5106 available from Varian Associates, Palo Alto, CA which is sold for use in mass spectroscopy and other applications in which very low, though uncontrolled, flow rates are required. An on/off valve 18 is also provided. This may be any one of a number of suitable valves such as the model 4BK, from Nupro, Inc., of Willoughby, Ohio. Valve 18 is connected by conduits to the leak 16 and to a large bulb 20 defining a known volume of gas. The gas pressure in the bulb 20 is monitored by a second pressure transducer 22, which may again be an MKS unit.

Operation of the apparatus shown in FIG. 1 is generally as follows. At the beginning of an adsorption experiment, the pressures in the bulb 20 and the sample chamber 12 are measured and recorded. The leak 16 is set to provide an orifice which is anticipated to provide a flow rate somewhat less than the probable equilibrium rate of adsorption/desorption, that is, such that the pressure in the chamber during flow is at all times an equilibrium pressure. The required flow rate will have been determined by preliminary experiments, experience of the operator, etc. Similarly, the aperture of the leak 16 required to provide a flow rate less than the anticipated equilibrium rate will have been determined in preliminary studies.

It is to be emphasized that, according to the invention, the rate at which gas is admitted by the leak 16 is not in any way actively "controlled" or varied, for example, to be constant or otherwise to permit calculation of the amount of gas admitted to the sample chamber based on the flow rate. The flow rate is simply limited by the leak so that the rate at which gas is admitted is always less than the equilibrium rate of adsorption/desorption. That is, at all times the rate of flow of gas into the sample chamber is so low that if flow were halted, no additional net adsorption would take place thereafter. Therefore, the partial pressure in the sample chamber 12 can at all times be safely assumed to be an equilibrium partial pressure.

As mentioned, an adsorption experiment commences with opening of on/off valve 18. Gas begins immediately to flow at a low rate controlled by the leak 16 from the bulb 20 into the sample chamber 12. Because, as noted above, the rate of flow is at all times less than the equilibrium rate of adsorption/desorption, the partial pressure within the sample chamber 12 is always indicative of a point on the isotherm. The pressure in the sample chamber 12 is measured at regular intervals of time, for example, every 100 ms, by means of pressure transducer 14. The pressure in the bulb 20 is similarly measured by means of pressure transducer 22.

The amount, that is, the number of moles, of gas which has flowed out of the bulb 20 at any time can be calculated by noting the change in pressure in the bulb 20 and by application of the ideal gas laws, which relate the change in pressure in a chamber of known volume to the change in the number of moles of gas present therein. The same volume of gas will have flowed into the sample chamber. However, as described above, some fraction of the gas will have been adsorbed on the sample 10. Therefore, the pressure within the sample chamber 12 as sensed by the pressure transducer 14 can be used to directly calculate the number of moles of gas which have been adsorbed by the sample, and thereby to calculate the surface area of the sample in accordance with the BET equation discussed above.

It will be appreciated that throughout this discussion and throughout the claims which follow, frequent mention is made of measurement of the pressures of gas in a particular vessel, especially as a step in calculation of the amount, that is, number of moles, of gas admitted to or withdrawn therefrom. Those of skill in the art will recognize that the temperature of a quantity of gas within a specific vessel also contributes to its pressure. Ideally, an entire experiment according to the invention is carried out at a single stable temperature, such that no compensation for temperature need be made; that is, so that the process is adiabatic. Those of skill in the art will recognize that to create and maintain a totally constant temperature over an entire experimental apparatus is a very difficult matter. Reference will be made below to various expedients which may be employed for control of temperature in the apparatus of the invention. Suffice it to say here that temperature will typically also be sensed with respect to all volumes in which pressure is measured, and that provision of appropriate compensation for variation in gas temperature, so as to provide corrected volumetric measurements where needed, is well within the skill of the art. Accordingly, all reference herein to measurements of pressure are to be read to include temperature control or compensation or both, as needed.

It will be appreciated from the above description of FIG. 1 that the adsorption technique proposed by the invention does not rely on control of the flow rate in order to enable calculation of the volume of gas admitted to the sample chamber 12 by multiplication of the flow rate by the time of admission. This of course is the method used in the Pieters et al., Bosch et al. and Innes disclosures described above. Avoidance of this expedient is a primary object of the invention, inasmuch as accurate control of flow is very difficult, particularly over a wide range of partial pressures. By comparison, the present invention permits extremely accurate calculations of the volume of gas admitted to the sample chamber 12 to be made by simply measuring the pressure in the bulb 20, a measurement which may be made accurately and readily with existing instrumentation. It is again also emphasized that the leak 16 is *not* used to control the flow rate to be constant or to take any particular value, only to ensure that it is at all times less than the equilibrium rate of adsorption/desorption. In this way, pressure measurements taken at any given time represent equilibrium conditions and can be used to determine points on the adsorption isotherm of the particular material for the particular gas being admitted.

Over some period of time, the pressure in the bulb 20 will become more or less equal to the pressure in the sample chamber 12. At this point, valve 18 may be closed and bulb 20 recharged to a higher pressure. The process then begins again with the opening of valve 18. At that time, the orifice of leak 16 may be further opened or closed, in accordance with the determination of an operator or in accordance with a pre-defined, computer-controlled sequence set up by the operator at the commencement of the experiment. The pressure in the sample chamber 12 at the beginning of this second phase of the experiment will ordinarily be the same as indicated by the last measurement of pressure made prior to the closing of valve 18 and recharging of bulb 20. If these pressure measurements differ, this indicates that the rate of admission of gas was greater than the equilibrium rate of adsorption/desorption, which will alert the operator that the experimental results from the first portion of the experiment are in question.

An adsorption experiment as described above may continue through a number of rechargings of bulb 20. When the partial pressure in the sample chamber reaches near unity, the gas will tend to condense within the sample chamber 12, and the adsorption isotherm can be completely plotted.

FIG. 2 shows the apparatus of the invention as arranged for desorption. The elements shown in FIG. 2 are essentially the same as those of FIG. 1, with the exception that a pump 24 may be added, and are similarly connected. The leak 16 is shown oppositely connected, to indicate that should a leak having directional sensitivity be used, its orientation must be reversed for desorption studies, as in desorption gas flows from the sample chamber 12 to the bulb 20. In operation of the apparatus of the invention in desorption, the bulb 20 is first evacuated with respect to the sample chamber 12. Typically, the sample 10 wil have been saturated to some degree with a desorbate gas. The pressures in the sample chamber 12 and bulb 20 are monitored by noting the signals output by pressure transducers 14 and 22. Upon opening of valve 18, gas in the sample chamber 12 begins to flow through the leak 16, which again is set so that the rate of flow is suitably less than the equilibrium rate of adsorption/desorption. After the valve 18 is opened, causing gas flow to commence, the pressures in bulb 20 and in sample chamber 12 are recorded at regular intervals of time. When the pressure of gas within the bulb 20 becomes sufficiently close to that in the sample chamber 12 that flow slows excessively, valve 18 may be closed and bulb 20 once again evacuated relative to sample chamber 12.

Pump 24 can be used at low pressures in the sample chamber, e.g., less than about 0.3 Torr, to urge further evacuation of the sample chamber 12. Gas pumped out of the sample chamber 12 by pump 24 is captured in bulb 20, so that even when pump 24 is employed, the volume of gas desorbed can be accurately measured. When the pressure over the sample is extremely low, the variable leak valve can be opened wide, such that only the pumping rate of the pump 24 will limit the rate of desorption of gas from the sample. At low pressures, this rate will still be slow enough that the sample will remain at equilbrium. This permits graphing of points on the isotherm directly from the pressures monitored by the pressure transducers 14 and 22. The amount of gas desorbed can be calculated by noting the pressure in the bulb 20 at any given time; by comparing this to the relative pressure of gas within the sample chamber 12, as measured by the pressure transducer 14, points on the desorption isotherm can be directly determined for the sample 10, and the surface area can be calculated using the BET equation.

As in the case of the adsorption studies discussed above in connection with FIG. 1, the leak 16 is not operated during desorption to control the rate of flow of gas in order that the amount of gas desorbed can be determined by multiplying the rate of flow by the time of flow. The amount of gas desorbed is calculated solely by monitoring changes in pressure in the bulb 20. This avoids the very significant limitations of the Bosch et al. and Pieters et al. methods discussed above.

In essence, and as noted above, Bosch et al's method is useful only over a very narrow range of partial pressures because outside this range the flow rate will not remain constant. The present invention provides an instrument which is useful over a wide range of partial pressures. According to the invention, the requirement that the flow rate be constant which is found in Bosch et al. is eliminated. This limitation on the Bosch et al device would be applicable to its use in both adsorption and desorption modes, although Bosch et al discuss only adsorption.

As noted above, Pieters et al. improved over Bosch et al. in that Pieters et al. discloses an active flow controller which allegedly controls flow to be accurate over a relatively wide range of inlet pressures. However, the Pieters et al. device still has some undesirable inaccuracies. Moreover, and more significantly, the Pieters et al. flow controller requires a minimum inlet pressure of approximately 15 Torr to function. Desorption at sample chamber pressures of less than 15 Torr therefore can not be controlled in any manner by the Pieters et al. device. This is a significant limitation; desorption analysis can only be performed using the Pieters et al. device with nitrogen as the desorbate gas (at a convenient temperature such as the temperature of liquid nitrogen), over a range of pressures between 760 and 15 Torr. The 0–15 Torr range is of extreme interest, and cannot be explored using the Pieters et al. device. The limitation is much more serious if analysis is to be performed using higher boiling point gases such as hydrocarbons and the like, in which the total pressure range of interest may be only from 80 to 0 Torr. In this case, the limitation of the Pieters et al. device to desorption analysis wherein the sample inlet pressure is above 15 Torr would render it almost useless for desorption studies of zeolitic catalysts and other samples of extreme interest.

As discussed briefly above, the present invention is useful in adsorption and desorption studies over a full range of partial pressures. The leak can be set to limit the flow rate to be less than essentially any equilibrium rate of adsorption/desorption and using any desorbate. Because there is no minimum sample chamber pressure which is needed for operation of the apparatus of the invention in desorption, desorption can theoretically be performed down to vanishingly small partial pressures. The ultimate limit on lower partial pressures which can be explored by the apparatus of the invention is a function of the ability of the pump 24 to provide a pressure differential on the sample which will cause gas to continue to be desorbed. In effect, performance of desorption studies down to sample chamber pressures of approximately $10^{-5}$ Torr can be anticipated.

As noted above, it is also sometimes of interest to perform adsorption studies using varying gases during the experiment. This is of interest, for example, in simulating refinery operations to determine the remaining useful life of a particular catalyst sample. Such studies are not possible using the apparatus of Pieters et al. because the Pieters et al. device must be calibrated separately for each species of gas to be used. This is because the Pieters et al. flow meter relies upon the thermal conductivity of the gas as a parameter in the operation of the flow meter. Because the thermal conductivities of specific gases vary widely, it is not possible to switch from one gas to another during an adsorption experiment without recalibration. The apparatus of the present invention is suitable for performance of such studies, as it does not require calibration for flow rate.

It will further be appreciated that in some cases it is desired to perform adsorption experiments in a "pulse" mode in which a pulse of gas is admitted to the sample chamber at a rate far higher than the equilibrium rate of adsorption. Desorption studies can similarly be performed. In such cases, the leak is momentarily bypassed or opened to a point that it does not restrict flow, admitting or removing a "pulse" of gas. The pressure in the sample chamber is then monitored over time. The time taken for the sample to equilibrate can be analyzed to determine certain characteristics of the pore structure of the sample, which may be of significant interest. The apparatus of the invention is admirably suited for such experiments. Again, a highly significant parameter is the amount of gas admitted to or removed from the sample chamber; according to the invention, this is determined simply by monitoring the change in the pressure of the gas within the bulb 20 and calculating the volume removed therefrom.

A final mode of operation of the invention, applicable to both adsorption and desorption studies, is the so-called "constant pressure" mode. In this mode, for example in an adsorption experiment, gas is admitted to the sample chamber continuously. The sample chamber pressure is monitored continuously and is used to control the variable leak, so that the pressure in the sample chamber remains relatively constant. This mode is of significant analytical interest, for example, in characterizing pore structures, simulating process environments, and the like. It should be appreciated that in this embodiment of the invention, while the flow rate is varied by control of the variable leak, the flow rate is not maintained at a known value, as is required by Pieters et al. Instead, the flow rate is permitted to take any value required to keep the pressure in the sample chamber relatively constant. In particular, it must be emphasized that no attempt is made to keep the flow rate constant in order to permit calculation of the amount of gas admitted as in Pieters et al. Instead, the amount of gas admitted is calculated by monitoring the change of pressure of the gas within the bulb 20.

It will be appreciated by those of skill in the art that varying the orifice provided by the variable leak 16 in order to control the pressure in the sample chamber to be relatively constant over time is a far simpler matter than controlling the orifice of a throttling valve to keep the flow rate constant over time, as in Pieters et al. In part, this simplification is realized because no calibration need be performed; the constant pressure can be chosen to be any value and the variable leak valve simply opened or closed slightly over time as needed to maintain this pressure constant. As described above, the Pieters et al. device requires separate calibration for each gas to be used. Moreover, of course, the accuracy of the results of Pieters et al. are highly dependent on this flow rate being constant over time.

Furthermore, control of the variable leak 16 to control the pressure to be constant over time involves a simple feedback arrangement from the transducer directly to the variable leak. Control of the Pieters et al. flow rate to be constant over time requires a very long and complex program for continually varying the aperture of the throttling valve over time, in accordance with values recorded during a calibration run. Should any experimental parameter depart from its value during the calibration run, the flow rate of Pieters et al. will be in error, while no means are provided for detecting or correcting this condition. According to this aspect of the present invention, this deficiency is completely eliminated in favor of a simple feedback arrangement of the sample chamber pressure for control of the orifice of the variable leak 16.

Desorption analysis may also be performed in the constant pressure mode; again, the orifice of the variable leak, which controls the rate of withdrawal of gas, is varied by stepper motor 15 responsive to the signal from pressure transducer 14, such that the pressure in the sample chamber 12 is maintained essentially constant over time. Again, this mode of operation of the apparatus of the invention is anticipated to be of great value in characterization of pore shapes and structures, which is of particular interest.

The flow rate of gas into and out of the sample chamber which occurs in performance of constant-pressure mode adsorption and desorption experiments respectively need not be limited to the equilibrium rate of adsorption or desorption.

FIG. 3 shows an overall schematic view of a preferred embodiment of the system of the invention. The apparatus shown is essentially similar to that described in connection with FIGS. 1 and 2. A number of additional apparatus elements are provided which allow the apparatus to be more versatile and amenable to more types of experimental procedures than would be the simple devices of FIGS. 1 and 2.

For example, four sample chambers 12 are shown in FIG. 3. These are connected by conduits and individual valves 30 to a manifold 32. First and second pressure transducers 34 and 36 are in communication with manifold 32. These pressure transducers are of significantly different ranges, for example, 0 to 1 Torr and 0 to 1,000 Torr. In this way, good resolution of the pressure can be obtained regardless of the actual pressure.

A variable leak 16 which may be opened or closed by means of a stepper motor 15 or the equivalent is shown in FIG. 3. In the constant-pressure mode, the stepper motor 15 is controlled by signals from a servo loop controller (SLC) 17, which compares a setpoint value for the chosen pressure to pressure signals from transducers 34 and 36, monitoring the pressure in the sample chambers 12. In this way the sample chamber pressure can readily be controlled to remain relatively constant, that is, equal to a target pressure defined by the setpoint.

An on/off valve 35 is on one side of the variable leak 16 in the line connecting the manifold 32 and the variable leak. This valve allows isolation of the sample from the variable leak 16 as needed.

First and second bulbs 38 and 40 are connected to the other side of variable leak 16. These are of substantially different size, for example, 10 ml and 100 ml. These are merely exemplary volumes and others may be employed as needed. The reason for providing differing volumes is so that a change in bulb pressure due, for example, to the flow of gas from the bulb into the sample chamber sample, is accurately detectable by pressure transducers 42 and 44. These again may be of substantially different ranges, for example, 0-1 Torr and 0-1,000 Torr, to ensure that a high resolution measurement of pressure can be made. Valves 45 and 46 control which of the bulbs 38 and 40 is connected to the leak 16.

Gases from sources indicated generally at 50 are also connected by way of valves 45, 46, 49 and 51 to bulbs 38 and 40. For example, in a nitrogen adsorption experiment, when refill of bulb 38 is needed, nitrogen will flow from source 50 into bulb 38 by opening valves 45 and 49. Valve 35 will be closed during refill. Subsequently valve 49 will be closed and valve 35 opened, permitting slow flow from bulb 38 into one of the sample chambers 12 via the corresponding valve 30. Monitoring of the pressure changes within the sample chamber 12 and bulb 38 will provide an indication of the amount of gas adsorbed.

Other gases may be admitted for various analytical purposes, as controlled by valve 51. The adsorbate gas can be varied during an experiment, as needed, and may be a relatively high boiling-point hydrocarbon or mixture of hydrocarbons. According to the invention, calibration for flow rate need not be performed, that is, regardless whether the thermal conductivity of the adsorbate gas varies, so that multiple-gas experiments are greatly simplified.

Desorption analysis using the complete system of FIG. 3 generally follows the process described above in connection with FIG. 2. A vacuum pump 52, which may be a diffusion pump, is connected, for example, to bulb 40, by way of conduits and valves 54 and 56. When the bulb 40 is evacuated to the desired degree, as measured by pressure transducer 44, valve 54 is closed and valve 35 opened, permitting gas to escape slowly from one of the sample chambers 12 via one of the valves 30 and the leak 16. As in the case of adsorption, the leak 16 controls the rate of gas leaving the sample chamber 12 containing the sample under study to a rate which is less than the equilibrium rate of adsorption/desorption of gas from the sample, such that the sample is always at equilibrium. Therefore, monitoring of the pressure in the sample chamber by means of pressure transducers 34 and 36 provides an equilibrium partial pressure measurement. Comparison of this value with the change of the pressure in bulb 40, as monitored by transducers 42 and 44, allows one readily to calculate the amount of gas which has been desorbed from the sample.

When the pressure in the sample chamber 12 becomes extremely low in desorption, for example, less then about 0.3 Torr, the orifice of variable leak 16 will present too much of a resistance to gas flow. At this time, values 35, 54, and 56 may be closed and the sample chamber connected to a much larger (typically 5 liter) bulb 60 by way of conduits as shown. Flow is controlled by valves 62 and 64. These valves and the associated piping will be quite large, e.g., $1\frac{1}{2}''$ in diameter, to allow free flow. Bulb 60 will have previously been evacuated to a very high degree by way of diffusion pump 52, possibly assisted by a forepump 66, connected by suitable conduits as indicated; this flow path is controlled by valves 68 and 70. When the pressure falls even lower, a second diffusion pump 72 connected by conduits between valve 64 and bulb 60 may be employed as a gas compressor to "pull" gas out of the sample chamber 12 and supply it to the bulb 60. The pressure in bulb 60 is monitored by a transducer 74. In this case, a single 0-1 Torr transducer will be sufficient.

The pumps 66 and 52 may also be used in pretreatment of the samples by way of a valve 76. Pretreatment of specific samples will be performed generally in accordance with known teachings. For example, a number of samples to be analyzed may be placed in chambers 12. These may then be individually placed in furnaces and heated to between 150° C. and 500° C., preferably to at least 400° C. At the same time, the sample chambers may be connected, e.g., to pumps 52 and 66, and evacuated to ensure that all volatiles are outgassed from the samples prior to their analysis. In this way, the pumps 52 and 66 can be used to serve dual purposes.

As discussed above, reference is made to measurement of gas pressure throughout this specification and in the appended claims. Those of skill in the art will recognize that the pressure of a given quantity of gas varies with its temperature. Therefore, means for very accurate temperature control or temperature compensation are required to ensure that the pressure measurements are either unaffected by temperature variation or are adequately compensated for such.

In the preferred embodiment of the system of the invention, both temperature control and temperature compensation will typically be employed. Each of the pressure transducers will be accompanied by a temperature transducer which can be used to monitor the temperature of the gas for temperature compensation. Suitable transducers are indicated schematically at 38a, 40a, and 60a. Selection and implementation of these transducers is within the skill of the art. The signals from the temperature transducers can be used to provide adequate compensation for the pressure signal due to variation in temperature; the compensation needed can be readily calculated using the gas laws. Temperature control is provided by placing as much of the apparatus in temperature-controlling baths as feasible. For example, all of the sample chambers 12 may be disposed in a liquid bath 80. Bulbs 38, 40 and 60 may be immersed in one or several separate water baths.

Typically bath 80 will contain liquid nitrogen, which may be controlled to remain at a relatively constant level by a level controller 82, connected to a valve 86 which controls flow of additional liquid nitrogen from a reservoir 84 into the bath 80. It will be appreciated, however, by those of skill in the art that even the best level controllers allow the liquid level to fluctuate somewhat. Furthermore, it will be appreciated that the temperature of the liquid nitrogen in the bath 80, if open to the atmosphere, as is usual, will change somewhat during the course of an experiment because of changes in the ambient atmospheric pressure and because of dissolution of oxygen in the liquid nitrogen from the surrounding air. Fluctuations in the level of the nitrogen in the bath 80 will vary the effective volume of the temperature controlled space. For example, as the level of nitrogen around the tubes connecting the sample chambers 12 to the valves 30 moves up and down, the temperature-controlled volume within will vary.

According to an important aspect of the invention, an auxiliary chamber 90 of the same proportions as the sample chambers 12 is also disposed in the bath 80 at the same level. Approximately 600 Torr of nitrogen is sealed into chamber 90. A further pressure transducer 92 is connected to monitor the pressure in chamber 90. Any change in liquid nitrogen level will be signaled by a change in the pressure sensed by transducer 92, and an appropriate compensation can be made to the pressure monitored within the sample chamber 12 containing the sample under analysis.

According to another aspect of the invention, the actual temperature of the liquid nitrogen within the bath is measured with the assistance of another auxiliary chamber 94 disposed in the bath 80, to which a further pressure transducer 96 is connected. Chamber 94 is filled with nitrogen until liquid nitrogen condenses therein. The pressure ($p_o$) above this liquid nitrogen inside this tube is measured by transducer 96 and accurately reflects the temperature of the liquid nitrogen bath. This is particularly important for size determination of pores larger than approximately 30 nm. These pores are filled near $p/p_o = 1$, such that an accurate measurement of $p_o$ is necessary. If the temperature of the liquid nitrogen bath changes in the course of an experiment, the signal from pressure transducer 96 can be used to appropriately compensate the signals from the transducer monitoring the pressure in the sample chamber 12.

The chambers 90 and 94 and their associated pressure transducers 92 and 96 thus together provide compensation for fluctuation in the level and the temperature of the bath 80 during the course of a given experiment.

In the preferred embodiment, the apparatus according to the invention is entirely controlled by a computer. The only manual operation is connection of the sample chambers containing the samples of the apparatus. The computer is shown in FIG. 3 in schematic form at 100. It controls the valves which control the flow of gas, and the pumps 52, 66 and 72. The connection of computer 100 to these devices is made by means of a digital-to-analog converter 102, which converts digital signals output by a control program running on the computer 100 to electrical signals suitable for controlling these devices. Signals from the pressure and temperature transducers are received by an analog-to-digital converter 104, which converts these electrical signals into data suitable for processing by a data acquisition program, which may run on computer 100, or on a separate computer. The interfaces 102 and 104 may be provided by a commercially available laboratory interface product, such as those produced by Computer Products, Inc. of Fort Lauderdale, Fla., under Model Nos. 7431, 7486, 7488, and 021-0033-012. The computer 100 may be a computer such as the PDP-11/44 of Digital Equipment Corporation. An alternative is provision of computer 100 as a part of an integrated laboratory automation system.

The software which controls the apparatus of the invention consists of two distinct sets of programs, the data acquisition programs and the control programs. The data acquisition programs typically sample all the various transducers at a given rate, e.g., ten times per second, and make no decisions. The data acquisition programs are completely independent of the control programs.

The control programs operate essentially independently of the data acquired by the data acquisition programs; however, data obtained by the data acquisition programs are occasionally needed by the control programs to make decisions. These control programs are responsible for the actual operation of the apparatus according to the invention. Responsive to operator-provided inputs, the control programs fill the reservoirs with gases at the desired pressures, implement the chosen modes of operation (which are discussed in detail below), and detect changes in the rate of adsorption or desorption, so that they can determine that the data density is appropriate.

The following is an example of raw data which may be stored by a data acquisition program:

TABLE 1

| | | Raw Data | | | |
|---|---|---|---|---|---|
| Mode | Time | P(reservoir) | P(sample) | P(Barom) | P(Level) |
| 1 | 0 | 10.534 | 0.0000 | 755.2 | 600.5 |
| 1 | 0.1 | 10.534 | 0.0000 | 755.2 | 600.5 |
| 1 | 5.1 | 10.143 | 0.0150 | 755.1 | 601.7 |
| 1 | 5.2 | 9.874 | 0.0180 | 755.1 | 598.3 |

The columns of Table 1 indicate, from left to right, the experimental mode selected, the time of sampling of the data, in seconds, and the pressures in the bulb containing the gas to be adsorbed, in the sample chamber 12 containing the sample to be analyzed, in chamber 94, and in chamber 90, all in Torr.

The data are then adjusted by the data acquisition program to take into account dead volume corrections, i.e. to compensate for the volume of the tubing connecting the various elements of the apparatus, and for pressure changes caused by changes in the liquid nitrogen level or ambient pressure. Furthermore, a choice can be made at this point concerning the density of the data to be retained, and the actual moles of gas absorbed can be calculated for further analysis.

Table 2 lists a typical form taken by the adjusted data. The data in the columns marked "P/Po" and "moles adsorbed" essentially represent points on the adsorption isotherm.

TABLE 2

| | Adjusted Data | | |
|---|---|---|---|
| Mode | Time | P/Po | Moles adsorbed |
| 1 | 0 | 0.000 | 0.000 |
| 1 | 1.0 | 0.001 | 0.001 |
| 1 | 5.0 | 0.015 | 0.010 |

At this point, the adjusted data will typically be transferred to a larger computer for subsequent analysis. This analysis can be accomplished with the help of one or more of the numerous published methods known to the art for the determination of BET surface area, pore-size distribution, diffusion analysis or other investigation appropriate for the task at hand.

FIGS. 4 through 10 provide flowcharts which schematically describe the steps in performance of adsorption and desorption experiments in several different modes according to the invention.

Figure 4:
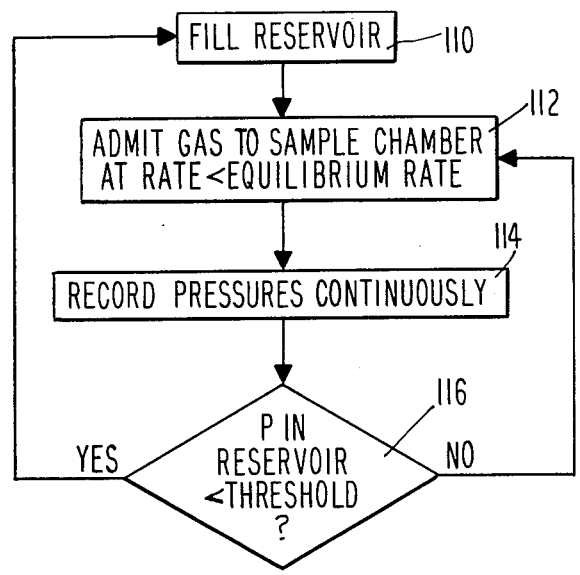
FIG. 4 shows a flowchart of the steps performed according to the invention in adsorption studies performed in the so-called "continuous" mode.

FIG. 4 shows the steps in performance of an adsorption experiment in the "continuous" mode, in which gas is admitted to the sample chamber continuously. The steps, broadly stated, begin with the step 110 of filling the reservoir; the reservoir may be either of bulbs 38 or 40 (FIG. 3). The sample will have been previously prepared for adsorption by outgassing at elevated temperature under vacuum, as generally described above, and as generally within the skill of the art.

At step 112, gas is admitted to the sample chamber at a rate less than the equilibrium rate of adsorbtion/desorption. As described above, this rate is controlled by the setting of the leak 16. It is emphased once again here that the orifice of the leak is not altered in order to keep the flow rate constant, for example, to enable calculation of the moles of gas admitted by multiplication of the flow rate times the time of admission. In fact, during the performance of a given experiment, the flow rate is likely to vary very greatly at the pressure differential between the reservoir and the sample chamber drops.

The pressure is recorded continuously in both the reservoir and the sample chamber during flow of gas from the reservoir to the sample chamber, as indicated at step 114. As discussed in connection with FIG. 3, the sample chamber and the reservoir are each connected to plural pressure transducers 34, 36 and 42, 44 respectively. Of these pairs, one of the transducers has a relatively wide range, such as 0 to 1,000 Torr, and the other a relatively narrow range, for example, 0 to 1 Torr. In this way very accurate pressure measurements can be made over a very wide range of pressures. The art of pressure measurement is such that measurements over a range of $10^{-5}$–1,000 Torr are possible using two pressure transducers.

At step 116, the pressure P in the reservoir is compared to a threshold value, predetermined by the operator, to determine whether it is time to recharge the reservoir. If the pressure is less than the threshold, the process is simply continued. If the pressure P is less than the threshold, refill is indicated and is performed as indicated at step 110.

At the end of a run, determined for example when the pressure in the sample chamber reaches an operator-determined stopping point, the data can be processed as outlined above to yield an adsorption curve.

At any time in the process, the on/off valve 35 may be closed. If the pressure in the sample chamber 12 then varies, this indicates that the gas flow rate is greater than the equilibrium rate of adsorption/desorption. The leak can be reset accordingly.

Figure 5:
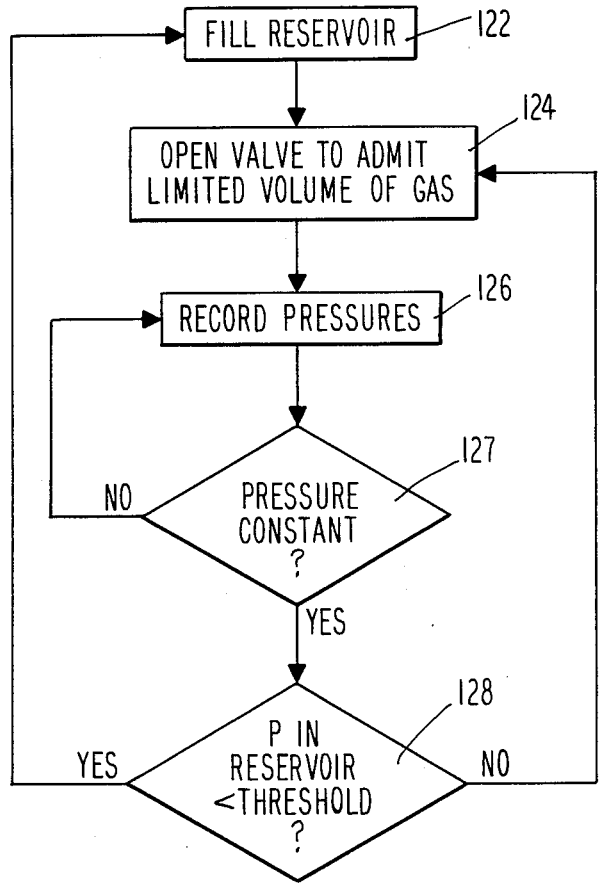
FIG. 5 shows a flowchart of the steps performed according to the invention in adsorption studies in the "pulse" mode.

FIG. 5 shows schematically the steps of an adsorption experiment performed in the so-called pulse mode, in which pulses of gas are admitted to the sample chamber at flow rates far higher than the equilibrium rate of adsorption or desorption. The pressure in the sample chamber is monitored as a function of time. When the pressure stops changing, equilibrium has been reached and a point in the isotherm can be graphed. The rate of gas diffusion into the sample is an indication of the pore structure of the sample.

The steps of this process are generally as follows. As in the case of the continuous mode described in connection with FIG. 4, an outgassed sample in a sample tube will have been supplied. The reservoir is filled as indicated at step 122. An on/off valve, e.g., valve 35 of FIG. 3, which is between the leak and the sample, is opened momentarily at step 124 to admit a limited volume of gas, essentially the volume of gas between the leak and the valve 35, to the sample chamber. The change in the pressure in the sample chamber is recorded as a function of time, as indicated at step 126. This step also includes the step of measuring the pressure in the reservoir, so that the total amount of gas admitted in the "pulse" can be determined. When the pressure in the sample chamber ceases to vary, as indicated at step 127, another pulse is withdrawn. Again, if the pressure in the reservoir is now below the threshold, as determined at 128, refill is performed; if not, a subsequent pulse can be admitted.

Figure 6:
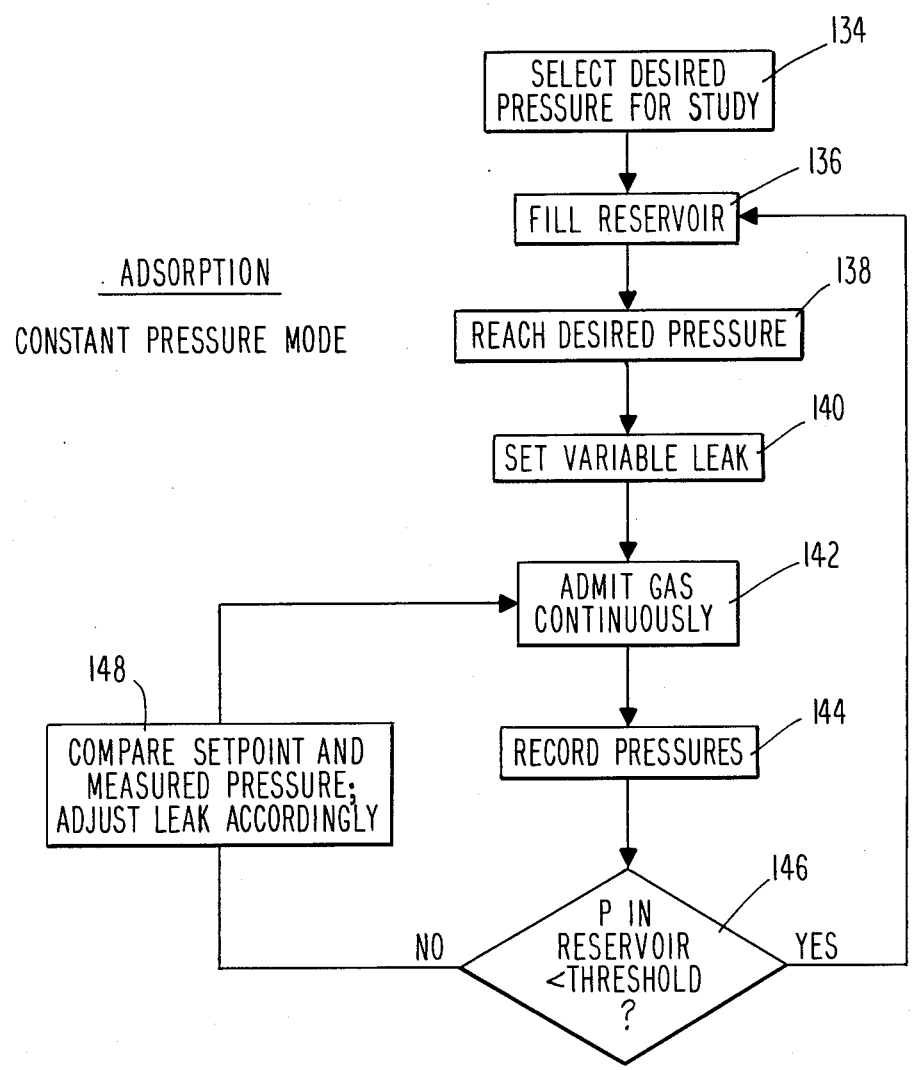
FIG. 6 shows a flowchart of the steps performed according to the invention in adsorption studies in a further "constant pressure" mode.

FIG. 6 shows the steps in operation of the apparatus of the invention in adsorption experiments performed in the constant pressure mode. In this case, as described briefly above, one selects a particular pressure for performance of adsorption studies in which the pressure in the sample chamber is maintained constant, at a value generally above the equilibrium pressure, such that adsorption goes on continuously. This involves gradual variation of the orifice of the leak. For example, over a period of some hours, the flow rate may gradually be reduced to zero as the catalyst becomes more fully saturated at the particular pressure. Continuous monitoring of the pressure in the bulb allows one to calculate the amount of gas admitted to the sample chamber, so that one can determine the amount actually adsorbed. This is of great significance in evaluation of certain pore structures and the like.

Constant-pressure adsorption studies begin at step 134 with the selection of a desired pressure for study by the operator; typically he will supply this to the control program as an experimental parameter. The reservoir is filled at step 136, and gas is admitted to the sample chamber until the desired pressure is substantially reached, as indicated at step 138. The variable leak 16 is set to a starting value at step 140. Gas is then continuously admitted to the sample chamber, as indicated at step 142. The pressures in the sample chamber and in the bulb are recorded at regular intervals of time, as indicated at step 144. The pressure in the sample chamber is used to determine the partial pressure over the sample, and the pressure in the bulb is monitored to calculate the amount of gas which has flowed into the sample chamber. In this case, however, the pressure from the sample chamber is also used to adjust the variable leak to maintain the pressure at the predetermined value. This step will typically involve comparison of the monitored pressure to a setpoint value, and adjustment of the leak accordingly, as indicated at step 148. For example, if the measured pressure is higher than the setpoint, the leak will be closed slightly; if lower, the leak will be opened somewhat. This step is typically performed after the reservoir pressure is compared to a threshold value at step 146. Again, if the reservoir pressure drops below the threshold value, valve 35 is closed, and the reservoir is refilled, for further experimentation.

At any point in any of the adsorption studies described above, the adsorbate gas can be varied as desired simply by refilling the reservoir with a differing gas for study. No recalibration is required. This provides additional experimental flexibility to the apparatus of the invention.

FIG. 7 shows the steps in desorption experiments as performed in the continuous mode. As described above, in this mode the leak controls the rate at which gas is withdrawn from the sample chamber to a rate less than the equilibrium rate of adsorption/desorption, such that the pressure within the sample chamber is always an equilibrium pressure. In this way, points on the isotherm can be derived from the pressure in the sample chamber at any time.

The process begins with the emptying of the reservoir at step 150, a sample having some amount of gas adsorbed thereon having previously been placed in the sample chamber. At step 152, valve 35 is opened, allowing gas to escape from the sample chamber to the reservoir at a rate limited by the leak to be less than the equilibrium rate of adsorption/desorption. The pressures in the reservoir and the sample chamber are recorded at regular intervals of times as indicated at step 154. At step 156, the reservoir pressure is compared to a threshold; if the reservoir pressure exceeds the threshold, the reservoir is evacuated as indicated at step 150. Otherwise, the process simply continues.

Again, it is to be emphasized here that the leak in this mode is not used to actively control the rate of withdrawal of gas from the sample chamber, but merely to ensure that it remains below a predetermined rate less than the equilibrium rate of adsorption/desorption.

FIG. 8 shows the steps in a desorption experiment performed in the "pulse" mode. In this case, gas is withdrawn from the sample chamber in pulses, that is, at flow rates higher than the equilibrium rate of adsorption/desorption. The sample chamber thereafter equilibrates as gas gradually desorbs. The desorption isotherm is significant to analysis of the pore structure.

Pulse mode desorption experiments begin with emptying of the reservoir as indicated at step 160. A valve between the reservoir and sample chamber is then opened momentarily in step 162 to release a limited amount of gas from the sample chamber into the relatively exhausted reservoir. (The leak is bypassed or opened to a point such that it does not restrict flow). The pressures in the reservoir and in the sample chamber are monitored at regular intervals of time as indicated at step 164. When the pressure in the sample chamber ceases to vary, indicating that equilibrium has been reached, as noted at step 165, another pulse is released. If the pressure in the reservoir is greater than a threshold pressure, as determined in step 166, the reservoir is evacuated again; if not, the valve is once again opened releasing another pulse.

Figure 9:
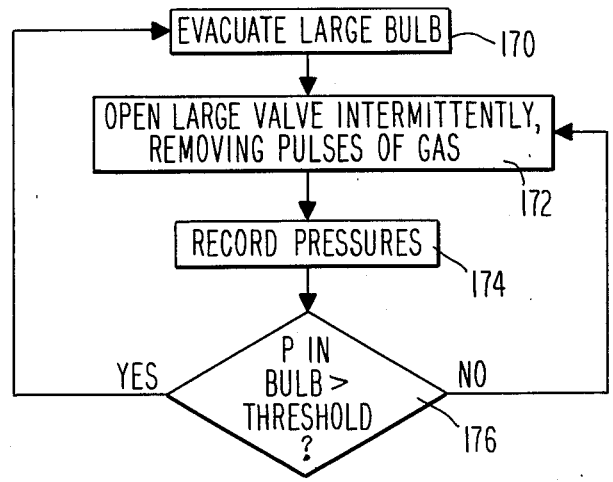
FIG. 9 shows a flowchart of the steps performed according to the method of the invention in desorption studies in the "low pressure" mode.

FIG. 9 shows a variation in desorption experimental techniques, applicable to both continuous and pulse modes, which comes into play at very low pressures in the sample chamber, e.g., less than about 0.1 Torr. At this point, the mean free path of the gas molecules is generally greater than the aperture of the orifice of the variable leak. The leak therefore slows the gas flow unacceptably, so that another path for withdrawn gas is needed. Typically, valve 35 will be closed and valve 62, of much larger diameter, will be opened, connecting the sample chamber and a large (5 liter) evacuated bulb 60. Pump 72, which may be a diffusion pump, is then used to remove gas from the sample chamber. The pressure in bulb 60 is monitored by transducer 74 to determine the total amount of gas desorbed by the sample. In this way, desorption experiments can be carried out at pressures envisioned to be as low as $10^{-5}$ Torr.

The steps in the low pressure process are shown schematically in FIG. 9. The large bulb 60 is evacuated at step 170. In the pulse mode, large valve 62 is opened intermittently, removing pulses of gas from the sample chamber, as indicated at step 172. The pressures in the bulb 60 and the sample chamber are recorded as functions of time, as indicated at step 174. When the pressure in the sample chamber equilibrates, the process is continued. In the constant flow mode, the valve 62 remains open, and gas is gradually withdrawn by pump 72 from the same chamber. In either case, when the pressure in the large bulb 60 becomes greater than a predetermined threshold pressure, as determined at step 176, the bulb is evacuated again. Otherwise, the large valve 62 is opened again and the process continues.

Figure 10:
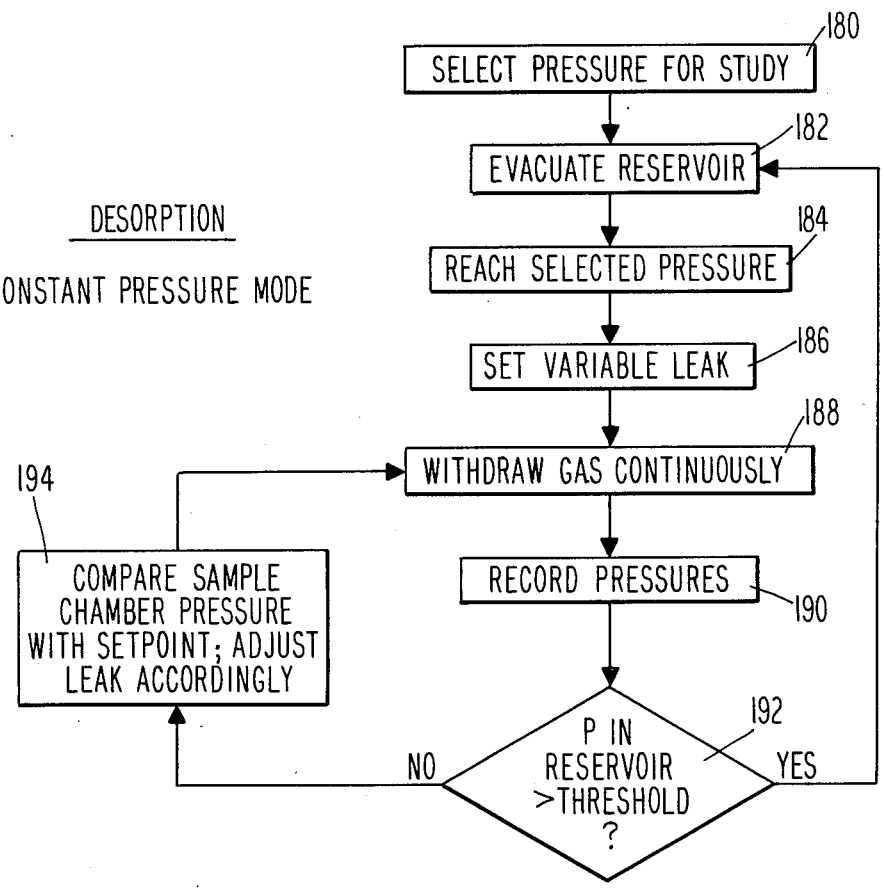
FIG. 10 shows a flowchart of the steps performed according to the method of the invention in desorption studies in the "constant pressure" mode.

FIG. 10 illustrates a desorption experiment carried out in the constant pressure mode. As in the case of constant pressure mode adsorption experiments, these experiments are performed with the sample chamber pressure remaining essentially constant; as discussed above, such constant pressure desorption studies can be of very significant interest in connection with evaluation of pore shape and size, and in connection with evaluation of particular catalysts, for example.

The process begins at step 180 with the selection of a particular pressure for study. A reservoir, which may be one of the smaller bulbs 38 or 40 or the large bulb 60, is evacuated as indicated at step 182. Gas is removed from the sample chamber until the selected pressure is substantially reached, at step 184. The variable leak is then set to an initial value in step 186. Gas is then withdrawn continuously, using the variable leak to limit the rate, as indicated at step 188. The pressures in the sample chamber and in the reservoir are recorded at frequent intervals of time, as indicated at step 190. If the reservoir pressure is greater than a threshold value, as indicated at 192, the reservoir is once again evacuated at 182. If not, the sample chamber pressure is compared to the setpoint; the leak is adjusted accordingly, as indicated at step 194.

It will be appreciated that, as in the case of the adjustment of the variable leak in performance of constant pressure mode adsorption experiments, the leak is not used to control the rate of gas flow to any particular rate, as proposed, for example, in the Pieters et al. patent discussed above. Instead, a simple servo-loop arrangement is provided to control the variable leak in direct response to the comparison of the pressure as sensed by the transducer monitoring the sample chamber pressure to the setpoint.

Implementation of this feedback arrangement in the preferred embodiment of the invention, in which the need for an operator's constant attention is avoided, involves providing means responsive to the sensed pressure for control of the variable leak. The control device may typically comprise a stepper motor 15 (FIG. 3) arranged to rotate, for example, the screw-threaded vernier control provided as part of the typical variable leak 16.

It will be appreciated that one way of implementing automatic control of the leak would be to provide this as an additional function of the computer 100 (FIG. 3). This would involve an exception to the general rule stated above to the effect that the data acquisition and control programs do not interact with one another. In this case, a data acquisition program would communicate the pressure value sensed by the transducers monitoring the pressure in the sample chamber to a control program for use in altering the setting of the variable leak. However, this exception to the general rule is an undesired complication on the data acquisition software.

According to the best mode of practice of the invention known to date, a separate feedback device, such as a servo loop controller (SLC) 17 (FIG. 3), will instead be provided with an input from one or more pressure transducers monitoring the pressure in the sample chamber 12. These transducers may typically be the same transducers 34, 36 used to provide inputs to the data acquisition program. The servo loop controller 17 can then simply compare this pressure to a set point input, and adjust the variable leak 16 accordingly by means of the stepper motor 15.

According to the best mode of practice of the application, the use of the variable leak 16 to control the pressure in the sample chamber 12 is thus readily accomplished by means of a simple feedback arrangement not involving the computer 100. Again, it will be appreciated that this is not equivalent to control of the rate of flow in response to measurement of the flow rate as disclosed in the Pieters et al. patent discussed above. Instead, the opening or closing of the variable leak is performed by comparison of the measured pressure to the setpoint.

It will be appreciated that there has been described an improved apparatus and methods for performing gas adsorption and desorption analysis on solids. According to an important aspect of the invention, all measurement or control of the flow rate of gas into or out of the sample chamber is eliminated in favor of other methods of measuring the amount of gas admitted or withdrawn.

More specifically, control of the flow rate in order to measure the amount of gas admitted has been eliminated in favor of simple measurement of the pressure change in a vessel of known volume, and calculation of the amount of gas admitted to or removed therefrom using the gas laws. Elimination of measurement and/or control of the flow rate thus avoids this technically troublesome problem. According to the invention, only the much simpler step of monitoring of pressure is performed; this is done using suitable pressure transducers which are commercially available and readily amenable to the purposes set forth herein.

The apparatus of the invention has been described in an environment which is suitable for entirely automatic control of the experimental apparatus by computer. Only simple control and data acquisition programs, well within the skill of the art, are required.

In a similar manner, generation of desired data, such as determination of the surface area of a sample, is possible using a wide variety of methods which are generally within the skill of the art, as generally suggested by the BET paper referred to above and other disclosures on related subjects. No particular means of processing the data to generate a desired experimental result has been set forth herein, as numerous suitable techniques are known to the art.

As described briefly above, it is to be understood throughout this specification and the appended claims that reference to measurement of gas pressure is to be understood to include control of the temperature of the gas and/or measurement of this temperature and appropriate compensation to the measured value of the pressure.

While a preferred embodiment of the invention has been described, it will be appreciated by those of skill in the art that numerous modifications and improvements thereon can be made without departing from its essential spirit and scope. Therefore, the present invention is not to be measured by the above exemplary disclosure, but only by the following claims.

What is claimed is:

1. Apparatus for measuring the amount of gas adsorbed by a sample, comprising:
   a first chamber of known volume;
   means for accurately monitoring the pressure of gas within said first chamber;
   a sample chamber of known volume;
   means for accurately monitoring the pressure of gas within said sample chamber;
   flow restrictor means connected between said chamber and said sample chamber; and
   means connecting said first chamber, said flow restrictor and said sample chamber for gas flow therebetween.

2. The apparatus of claim 1 wherein said flow restrictor means comprises an orifice which limits gas flow therethrough to a rate less than the equilibrium rate of adsorption/desorption of said gas with respect to a particular sample material.

3. The apparatus of claim 2 further comprising on/off valve means disposed between said first chamber and said sample chamber.

4. The apparatus of claim 3 further comprising supply means for supplying gas to said first chamber.

5. The apparatus of claim 4 further comprising computer means for controlling the operation of said on/off valve and of said supply means for controlling the supply of gas to said first chamber.

6. The apparatus of claim 5 wherein said computer means additionally comprises means for recording the temperature and pressure within said first and sample chambers.

7. The apparatus of claim 2 wherein said apparatus further comprises controller means, and wherein said flow restrictor means is controllable by said controller means to vary the size of said orifice, said controller means being responsive to signals received from said means for accurately monitoring the pressure of gas in said sample chamber and comprising means for controlling said orifice in order to maintain the pressure of gas in said sample chamber essentially constant over time.

8. The apparatus of claim 7 wherein said controller means comprises servo loop controller means adapted to compare the pressure of gas in said sample chamber to a setpoint and for controlling said orifice in response to said comparison.

9. The apparatus of claim 1, wherein said sample chamber is disposed within a bath of liquid, said bath comprising level controller means and liquid supply means for replenishing the level of liquid in said bath as needed, and comprising means for monitoring the level of said bath and for providing a corresponding compensation signal, said monitoring means comprising an auxiliary chamber physically similar to said sample chamber and disposed at the same level in said bath as said sample chamber, and pressure transducer means for providing a signal responsive to the pressure within said auxiliary chamber, whereby variations in the level of fluid within said bath may be identified by monitoring the signal from said pressure transducer means.

10. The apparatus of claim 9 further comprising means for monitoring ambient pressure and temperature, comprising a further auxiliary chamber disposed in said bath and containing a fixed amount of gas, and pressure transducer means for monitoring the pressure of said gas in said further auxiliary chamber, wherein variation in ambient pressure or ambient temperature may be detected by monitoring the pressure in said further auxiliary chamber, whereby compensation may be made therefor.

11. Method for measuring the amount of gas adsorbed by a sample, comprising the steps of:
disposing said sample in a first sample chamber of known volume;
measuring the pressure of gas within said first chamber;
measuring the pressure of gas within a second chamber of known volume;
creating a flow path between said first sample chamber and said second chamber through a flow restrictor having an orifice therein sized such that the rate of gas flow therethrough is less than the equilibrium rate of adsorption/desorption of gas with respect to said sample;
monitoring the changes in gas pressure in said chambers as gas flows through said flow path from said second chamber into said sample chamber and is adsorbed by said sample; and
determining the amount of gas adsorbed by said sample as a function of the changes in pressure in said first and second chambers.

12. The method of claim 11, comprising the additional steps of comparing the pressure in said second chamber to a threshold value, and when said pressure falls below said threshold value, halting the flow of gas from said second chamber into said sample chamber and admitting additional gas to said second chamber.

13. Method for measuring the amount of gas desorbed from a sample, comprising the steps of:
disposing a sample having a quantity of gas adsorbed thereon in a sample chamber of known volume;
measuring the pressure of gas within said sample chamber;
measuring the pressure of gas within a second chamber of known volume evacuated relative to said sample chamber;
creating a flow path between said sample and second chambers through a flow restrictor having an orifice sized such that the rate of flow of said gas from said sample chamber to said second chamber is less than the equilibrium rate of adsorption/desorption of gas with respect to said sample;
monitoring the changes in pressure in said chambers as gas is desorbed from said sample and flows from said sample chamber into said second chamber; and
determining the volume of gas desorbed from said sample as a function of changes in pressure in said chambers.

14. The method of claim 13 comprising the additional step of further evacuating said second chamber when the pressures in said chambers approach equality.

15. Method for performing adsorption studies at constant pressure, comprising the steps of;
disposing a sample in a first chamber of known volume;
measuring the pressure of gas within said first chamber;
measuring the pressure of gas within a second chamber of known volume;
creating a controllable gas flow path between said first chamber and said second chamber through a controllable flow restrictor having a variable orifice therein;
monitoring the change in gas pressure in said second chamber as a function of time;
monitoring the change in gas pressure in said first chamber as a function of time;
controlling the orifice of said flow restrictor responsive to said measurements of the pressure in said first chamber such that the pressure in said first chamber remains substantially constant over time; and
determining the amount of gas adsorbed by said sample at any given time as a function of the pressures in said first and second chambers.

16. Method for performing desorption studies at constant pressure, comprising the steps of:
disposing a sample having a quantity of gas adsorbed thereon in a first chamber of known volume;
measuring the pressure of gas within said first chamber;
measuring the pressure of gas within a second chamber of known volume;
creating a controllable gas flow path between said first sample chamber and said second chamber through a controllable flow restrictor having a variable orifice therein;
monitoring the change in gas pressure in said second chamber as a function of time;
monitoring the change in gas pressure in said first chamber as a function of time;
controlling the orifice of said flow restrictor responsive to said measurements of the pressure in said first chamber such that the pressure in said first chamber remains substantially constant over time; and determining the amount of gas desorbed by said sample at any given time as a function of the pressures in said first and second chambers.

17. Apparatus for measuring the amount of gas desorbed by a sample, comprising:
   a first chamber of known volume;
   means for accurately monitoring the pressure of gas within said first chamber;
   a sample chamber of known volume;
   means for accurately monitoring the pressure of gas within said sample chamber;
   flow restrictor means connected between said first chamber and said sample chamber; and
   means connecting said first chamber, said flow restrictor means and said sample chamber for gas flow therebetween.

18. The apparatus of claim 17 wherein said flow restrictor means comprises an orifice which limits gas flow therethrough to a rate less than the equilibrium rate of adsorption/desorption of said gas with respect to a particular sample material.

19. The apparatus of claim 18 further comprising on/off valve means disposed between said first chamber and said sample chamber.

20. The apparatus of claim 19 further comprising vacuum pump means for evacuation of said first chamber.

21. The apparatus of claim 20 further comprising computer means for controlling the operation of said on/off valve and of said vacuum pump means.

22. The apparatus of claim 21 wherein said computer means additionally comprises means for recording the temperature and pressure within said first and sample chambers.

23. The apparatus of claim 22 wherein said apparatus further comprises controller means, and wherein said flow restrictor means is controllable by said controller means to vary the size of said orifice.

24. The apparatus of claim 23 wherein said controller means comprises servo loop means adapted to receive signals from said means for accurately monitoring pressure of gas in said sample chamber, to compare said signals to a setpoint, and to control said orifice responsive to said comparison.

25. The apparatus of claim 17, wherein said sample chamber is disposed within a bath of liquid, said bath comprising level controller means and liquid supply means for replenishing the level of liquid in said bath as needed, and comprising means for monitoring the level of said bath and for providing a compensation signal therefor, said monitoring means comprising an auxiliary chamber physically similar to said sample chamber and disposed at the same level in said bath as said sample chamber, and pressure transducer means for providing a signal responsive to the pressure within said auxiliary chamber, whereby variations in the level of fluid within said bath may be identified by monitoring the signal from said pressure transducer.

26. The apparatus of claim 25 further comprising means for monitoring the ambient pressure and temperature, comprising a further auxiliary chamber disposed in said bath and containing a fixed amount of gas, and pressure transducer means for monitoring the pressure of said gas in said further auxiliary chamber, wherein variation in ambient pressure or ambient temperature may be detected by monitoring the pressure in said further auxiliary chamber, whereby compensation may be made for variation in ambient temperature or pressure.

27. Apparatus for performance of adsorption and desorption experiments, comprising:
   sample chamber means for receiving a sample of material;
   a chamber of known volume for receiving a gas to be employed in said adsorption and desorption experiments;
   pressure transducer means connected to each of said sample chamber means and said chamber of known volume, to monitor the pressures therein; and
   a flow restrictor connected between said sample chamber means and said chamber of known volume, for limiting the rate of flow of gas therebetween.

28. The apparatus of claim 27 wherein said flow restrictor comprises an orifice which is sized to limit flow of gas therethrough to a rate less than the equilibrium rate of adsorption/desorption of said gas with respect to a particular sample material.

29. The apparatus of claim 28 further comprising pump means for evacuating said chamber of known volume with respect to said sample chamber prior to removal of gas from said sample chamber in performance of desorption studies.

30. The apparatus of clam 27 wherein said sample chamber means is temperature controlled.

31. The apparatus of claim 30 wherein said sample chamber means is temperature controlled by immersion thereof in a liquid bath.

32. The apparatus of claim 31 wherein said liquid bath comprises level controller means for keeping the level of liquid in said liquid bath relatively constant over time.

33. The apparatus of claim 32, comprising a further chamber disposed in said bath, said further chamber having the same physical configuration and being of the same material as said sample chamber means, and additional pressure transducer means connected to said further chamber disposed in said bath, for providing an indication of liquid level in said bath.

34. The apparatus of claim 33 wherein a plurality of sample chamber means are provided, each of said sample chamber means being immersed in said bath, and each of said sample chamber means being connected to a manifold by individual valve means.

35. The apparatus of claim 27 wherein a plurality of said chambers of known volume are provided, each being of differing volume.

36. The apparatus of claim 27 further comprising computing means for storing data provided by said pressure transducers and for controlling the flow of gas between said sample chamber means and said chambers of known volume.

37. The apparatus of claim 27 further comprising means for monitoring pressure within a sample chamber and for controlling the orifice of said flow restrictor means responsive thereto, such that the pressure in said sample chamber may be maintained substantially constant during adsorption or desorption experiments.

* * * * *